(12) United States Patent  
Glaser-Seidnitzer et al.

(10) Patent No.: US 8,365,087 B2
(45) Date of Patent: Jan. 29, 2013

(54) METHOD AND USER INTERFACE FOR THE GRAPHICAL PRESENTATION OF MEDICAL DATA

(75) Inventors: Karlheinz Glaser-Seidnitzer, Fuerth (DE); Johannes Kling, Zurich (CH); Diana Martin, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 373 days.

(21) Appl. No.: 12/420,237

(22) Filed: Apr. 8, 2009

(65) Prior Publication Data

US 2009/0276725 A1 Nov. 5, 2009

(30) Foreign Application Priority Data

Apr. 8, 2008 (DE) .......................... 10 2008 017 845

(51) Int. Cl.
*G06F 3/048* (2006.01)
*A61B 5/05* (2006.01)
(52) U.S. Cl. ........ 715/771; 715/762; 715/763; 715/764; 600/411; 600/421
(58) Field of Classification Search .................. 382/128; 715/781, 838, 762–764, 771; 600/421, 411
See application file for complete search history.

(56) References Cited

U.S. PATENT DOCUMENTS

| | | | | |
|---|---|---|---|---|
| 5,452,416 A * | 9/1995 | Hilton et al. | .................. | 715/783 |
| 5,954,650 A * | 9/1999 | Saito et al. | .................... | 600/425 |
| 5,987,345 A * | 11/1999 | Engelmann et al. | .......... | 600/407 |
| 6,785,410 B2 * | 8/2004 | Vining et al. | ................. | 382/128 |
| 7,058,901 B1 * | 6/2006 | Hafey et al. | ................... | 715/792 |
| 7,170,532 B2 * | 1/2007 | Sako | ............................. | 345/637 |
| 7,489,810 B2 * | 2/2009 | Owen | .......................... | 382/128 |
| 7,787,672 B2 * | 8/2010 | Reicher et al. | ................ | 382/128 |
| 7,890,498 B1 * | 2/2011 | Hafey et al. | ................... | 707/722 |
| 2002/0101436 A1 * | 8/2002 | Shastri et al. | ................ | 345/619 |
| 2002/0115282 A1 * | 8/2002 | Lin et al. | ....................... | 438/622 |
| 2002/0183607 A1 * | 12/2002 | Bauch et al. | ................. | 600/407 |
| 2007/0078306 A1 * | 4/2007 | Allison et al. | ............... | 600/300 |
| 2007/0078674 A1 * | 4/2007 | Weinberg et al. | ................ | 705/1 |

(Continued)

FOREIGN PATENT DOCUMENTS

DE 101 58 226 A1 5/2003

OTHER PUBLICATIONS

"An Authorizing System for Multidimensional Documents," Wüthrich, Computer Science Theory Laboratory, Swiss Federal Institute of Technology (1998).

(Continued)

*Primary Examiner* — Tadeese Hailu
(74) *Attorney, Agent, or Firm* — Schiff Hardin LLP

(57) ABSTRACT

A method and a user interface for the implementation of a medical examination with at least one imaging device operated by determination and input of a group of measurement parameters via an input device of the user interface, generation of spatially resolved image information with the at least one imaging device depending on the group of measurement parameters, and storage of the image information on a storage medium, presentation of the image information as a data symbol on a screen of the user interface, Multiple data symbols are presented in a predetermined arrangement on the screen for a medical assessment. In order to be able to clearly present all data of a patient that are acquired in imaging methods in an accessible and manipulable manner, the data symbols are arranged on the screen by a control unit depending on at least three display parameters.

11 Claims, 4 Drawing Sheets

U.S. PATENT DOCUMENTS

2007/0115282 A1* 5/2007 Turner et al. ............... 345/424
2007/0130165 A1* 6/2007 Sjoblom et al. ............. 707/10
2007/0130515 A1 6/2007 Maas
2008/0126982 A1* 5/2008 Sadikali et al. ............. 715/810
2008/0269609 A1* 10/2008 Abend et al. ............... 600/440
2009/0080719 A1* 3/2009 Watt ........................... 382/128

OTHER PUBLICATIONS

"LifeLines: Using Visualization to Enhance Navigation and Analysis of Patient Records," Plaisant, et al., Proc. of the AMA Symposium (1998).

* cited by examiner

METHOD AND USER INTERFACE FOR THE GRAPHICAL PRESENTATION OF MEDICAL DATA

BACKGROUND OF THE INVENTION

1. Field of the Invention

The present invention concerns the graphical presentation of medical examination results that were acquired with imaging methods, and in particular a method and a user interface for the implementation of a medical examination.

2. Description of the Prior Art

For the necessary categorization, sorting and evaluation of data acquired in imaging methods of medical technology, not only are the spatial dimensions (such as 3D data sets, slice images, body region) relevant, but also time information such as the chronological order of the acquisitions (acquisition points in time), as well as information that results from the examination context, such as the employed imaging method, the scanner model and the medical question. The relevance of such factors to the task of the user can change from one moment to the next, even multiple times in one application situation under the circumstances. User interfaces that enable access to radiological data sets should allow presentation of multiple factors and enable an optimally fast and uncomplicated interaction.

Known user interfaces in the form of browsers for radiological data sets are typically designed for a specific user situation. For example, in the prior art, in a simple hierarchical categorization, a sorting according to patient name is conducted on a first hierarchical level, a sorting according to the examination designation is conducted on a second hierarchical level, a sorting according to the designation of the image series is conducted on a third level and a sorting according to individual images is conducted on a fourth level A visual presentation is possible only in the fourth level; interaction with the data set (for example adjustment of contrast/brightness) is possible only after the user has selected and loaded an image series.

The access to image series therefore is forced to occur in serial interactions and is associated with relative high cognitive effort and time on the part of the user.

SUMMARY OF THE INVENTION

An object of the present invention to provide a user interface of a browser for data objects with which all data of a patient that are acquired in imaging methods can be clearly presented on a screen such that they can be accessed and manipulated.

The basis of the invention is to expand the browser for presentation of the radiological data sets in multiple (spatial and contextual) dimensions, and these multiple dimensions are simultaneously made easily accessible and switching among the different dimensions is enabled with little effort.

The method according to the invention for the implementation of a medical examination via a user interface of at least one imaging device includes the steps of determination and input of a group of measurement parameters via an input device of the user interface, generation of spatially resolved image information with the at least one imaging device depending on the group of measurement parameters, and storage of the image information on a storage medium; presentation of the image information as a data symbol on a screen of the user interface. Multiple data symbols are presented in a predetermined arrangement on the screen for a medical assessment with the data symbols arranged on the screen by a control unit depending on at least three display parameters.

In the embodiments of the method, one or more of the following features can be included:

the three display parameters correspond to three spatial dimensions of a miniature view,
  the multiple data symbols are arranged in a grid with three display parameters, wherein: the first display parameter is a time parameter, the second display parameter is an imaging device parameter and the third display parameter is an examination parameter,
  the time parameter corresponds to the point in time of the image acquisition, such that the multiple data symbols are shown sorted in chronological order,
  the imaging device parameter designates the type and/or setting parameters of the imaging device,
  the examination parameter designates the examined body region of the patient,
  the method comprises the step: influencing the position of a pointer symbol on the screen via an electromechanical transducer to select one or more data symbols and/or display parameters, wherein the size of the multiple display parameters depends on their distance from the pointer symbol on the screen,
  the time parameter assumes year dates as a value,
  upon activation of the user interface, those of the multiple data symbols that belong to the most recent year are emphasized,
  those of the multiple data symbols that belong to the most recent year at least partially occlude adjacent data symbols.

A corresponding device according to the invention for implementation of a medical examination has at least one imaging device for the generation of spatially resolved image information depending on at least one measurement parameter, a storage medium for storage of the image information thereupon; and/or a screen for the presentation of the image information as a data symbol thereupon. Multiple data symbols are shown in a predetermined arrangement on the screen for a medical assessment and a control unit causes the data symbols to be arranged on the screen depending on at least three display parameters.

The device is advantageously provided with an electromechanical transducer to influence the position of a pointer symbol on the screen to select one or more data symbols and/or display parameters, with the size of the display parameters being determined by the control unit depending on their distance from the pointer symbol on the screen.

An advantage of the invention is that the view of the data sets can be adapted very quickly to the respective usage context (the question posed by the user). Moreover, the user operates with data symbols (thumbnails), thus visual representations with which he can also interact. It is to be assumed that such a mode of operation accommodates visually oriented people. Moreover, the use of the invention is apparent in that image series/data sets can be presented in an easily accessible manner with the possibility to leaf through or play them back quickly. The presentation can be adapted without further measures to various questions; the screen space can always be optimally utilized.

DESCRIPTION OF THE PREFERRED EMBODIMENTS

Figure 1:
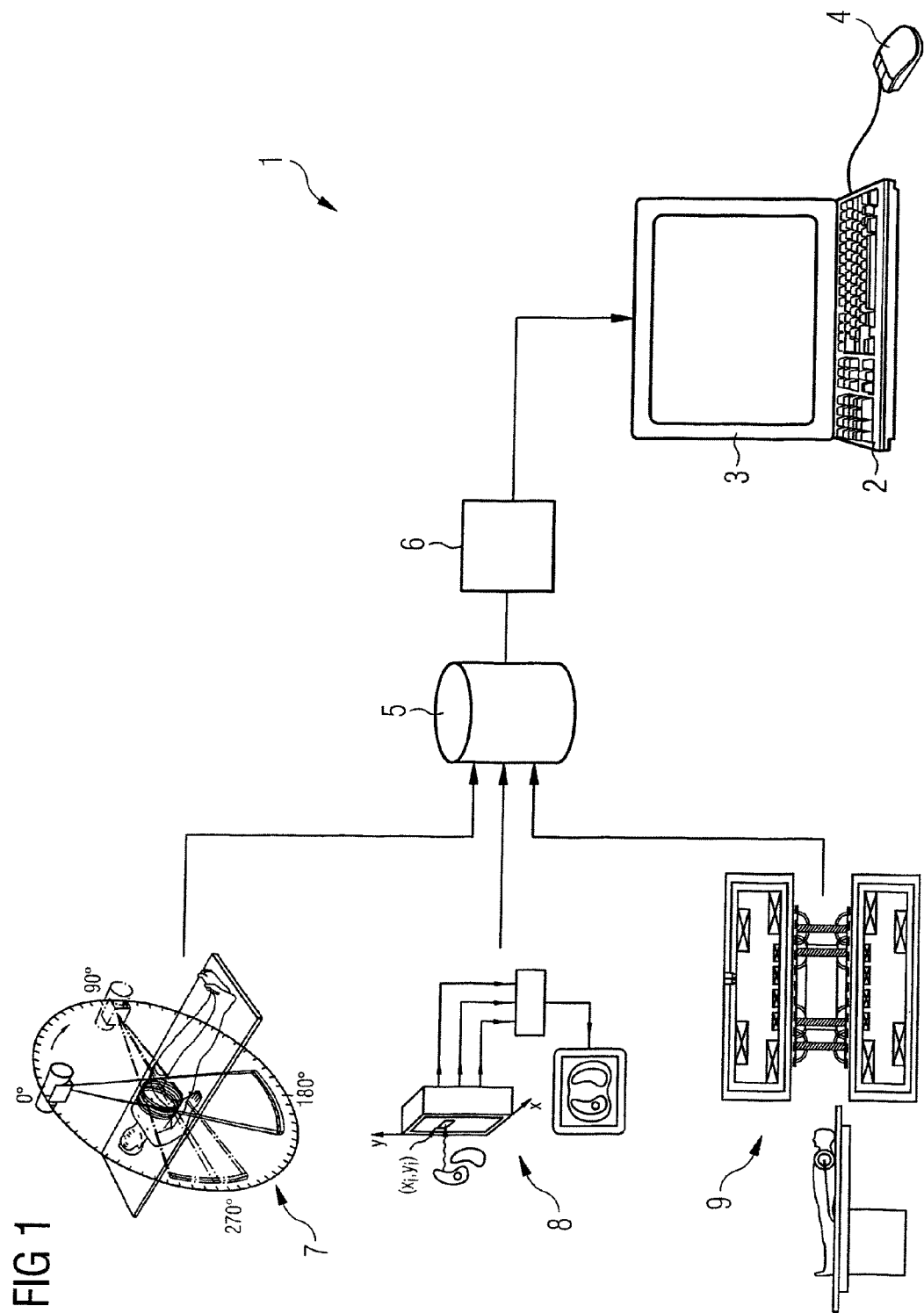
FIG. 1 schematically shows the design of an embodiment of the user interface according to the invention.

The presentation in figures is not to scale; identical elements or elements having identical effects are provided with the same reference characters.

The user interface according to the invention utilizes the possibilities of two-dimensional presentation under consideration of established parameters in the display of data symbols and thus provides the user an overview of all present image series of a single patient in the form of a two-dimensional diagram: for example, all years in which image series were generated are displayed in parallel. These are sorted according to the respective modality (imaging method).

The first classification can be conducted so that a rectangle is created for each year. Data symbols that correspond to the image series are displayed in these rectangles; said image series are retrieved and shown at a suitable size when the corresponding data symbol has been selected. The most recent year is focused on (emphasized) by default, so that its objects can be presented with the largest available height and width. The remaining data symbols are accordingly shown smaller. This can proceed so far that the direct neighbors are partially occluded.

If the user would like to compare multiple images with one another, he can freeze the current focus. The focused object remains at its position and at the current size; all other objects redistribute, wherein the space reserved for the frozen image is not involved. The user can now focus on other images and naturally also freeze even more images in order to compare them one another.

The realization of this technical teaching is explained in the following using Figures.

FIG. 1 shows an embodiment of the user interface 1 according to the invention. The user interface 1 comprises an input device 2 for the specification of measurement parameters by the user. This interactive setting of the measurement parameters as well as the measurement result are displayed on the screen 3 of the user interface. The user is assisted in the setting of parameters and in the selection of parameters or, respectively, shown objects by an electromechanical transducer, for example, a computer mouse 4, or a trackball (not shown) or other suitable devices.

For implementation of the display function of the user interface 1, data are retrieved from a storage medium 5 and then displayed on the screen 3. The display is controlled in accordance with the invention by a special control device 6. This presentation of objects on the screen 3 is explained further below using FIGS. 3 and 4.

The data on the storage medium 5 that are displayed on the screen 3 at an arbitrary point in time were acquired with one of three imaging methods and are present as a result of a computed tomography (CT) acquisition 7, or as a result of a positron emission tomography (PET) acquisition 8, or as a result of a magnetic resonance (MR) acquisition 9. Two methods can thereby also be combined with one another, for example PET and CET into PET-CT.

The data from one or more of the imaging methods 7, 8, 9 indicated in FIG. 1 are displayed on the screen 3. The display depends on preset display parameters. These display parameters can in principle be selected independently; their number is also not predetermined in advance.

Figure 2:
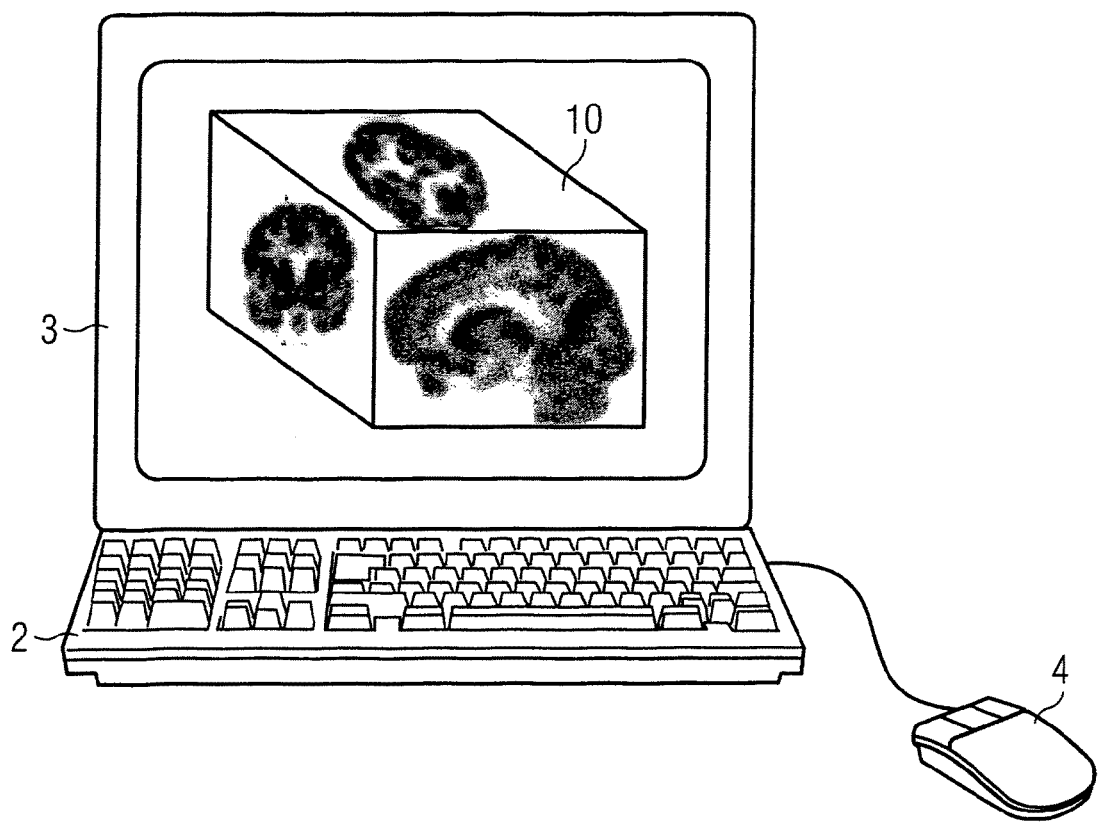
FIG. 2 schematically shows an example for a display on the user interface according to the invention.

A first example for the display of measurement results that are stored on the storage medium 5 is shown in FIG. 2. There three display parameters are selected that correspond to the three spatial coordinates. In this case, for example, the exposure of a brain (acquired with the PET method 8, for example) in a sagittal view (bottom left), in a transaxial view (top right) and in a coronal view (top left) is presented as a data symbol 10 on the screen 3 of the user interface. Given corresponding graphical power of the user interface, this presentation can be expanded to the extent that a real three-dimensional image is generated. The image can then be rotated as necessary in multiple directions (not shown) via input of spatial coordinates via the electromechanical transducer device 4. The data symbol 10 is therefore a first presentation of the spatially resolved image information on the storage medium 5 that can be interactively manipulated by the user via activation via the computer mouse 4 or the keyboard 2.

Figure 3:
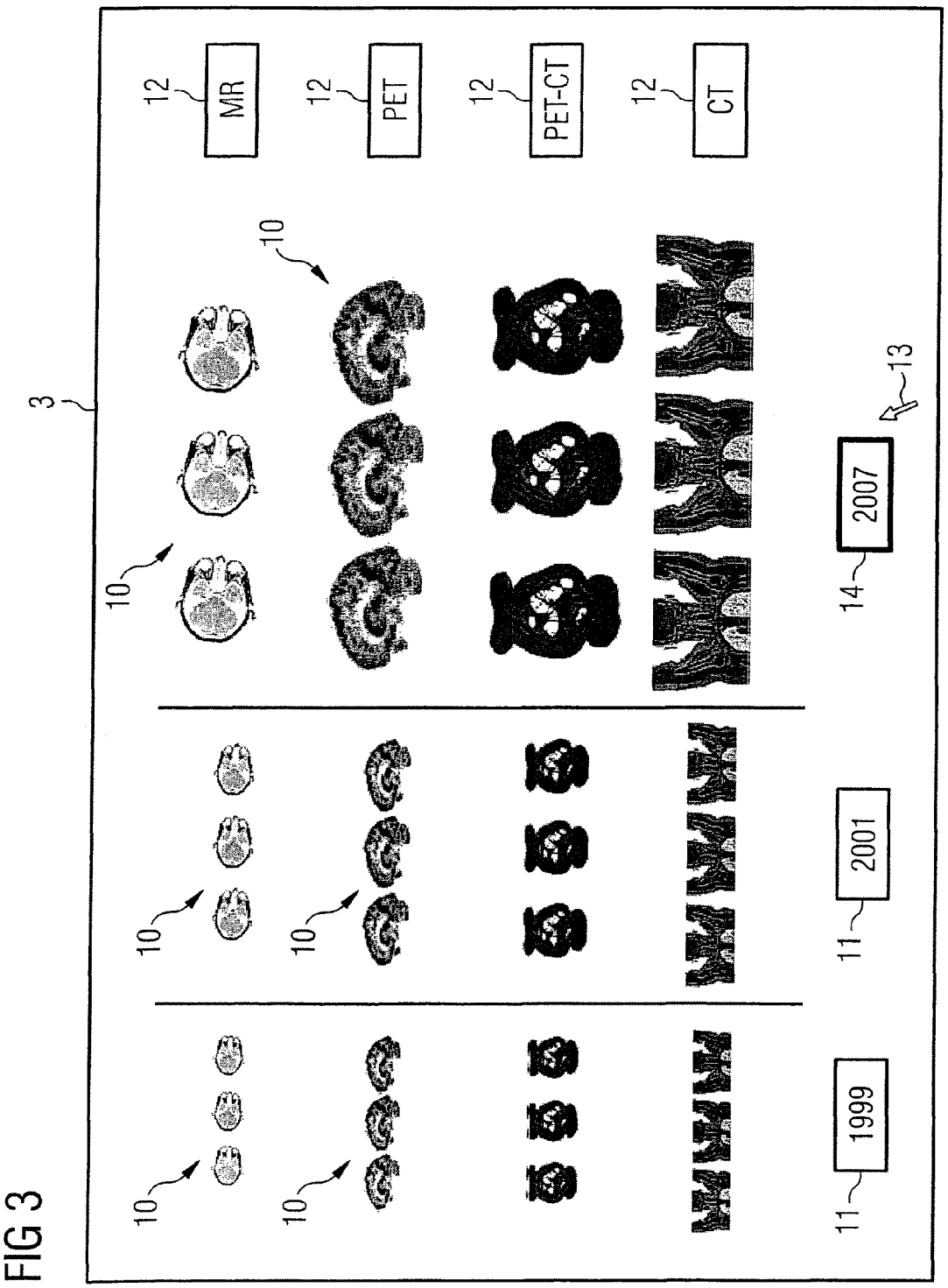
FIGS. 3 and 4 show additional examples for the presentation of patient information according to the invention on the screen of a user interface according to the invention.

However, the interactive manipulation of the spatially resolved image information is not limited to the rotation or displacement in space. It is likewise just as easily possible to simultaneously display and interactively manipulate more than three dimensions. This is explained in the following using FIGS. 3 and 4. The screen 3 of the user interface 1 is respectively shown in FIGS. 3 and 4. In FIG. 3, image sequences are shown that were acquired with a specific imaging method. In the rows, those images are assembled that were acquired with the same imaging method. Those images that have the same acquisition time period as a measurement parameter are assembled in each column. Here, among other things, the "granularity" of the parameter values is to be taken into account (among other things), which is explained in detail further below. A series of images that were acquired with the MR method 9 is shown in the first row in FIG. 3. The series of images can comprise arbitrarily many individual images; here three images are respectively shown as data symbols 10 that should be differentiated depending on an examination parameter, i.e. one of multiple measurement parameters. For example, the examination parameter can indicate the height of the observation level along the body axis (lower skull region or upper skull region). Or, exposures can have been produced after the administration of various medicines. Such a series of exposures is indicated here by three images, wherein these can naturally be more or fewer than three images. The cited assessment parameter is not explicitly shown in Figures; however, it is innately understood that it is the central measurement parameter for the medical analysis of the image information.

A first series of such MR exposures of the respective patient was made in 1999. The year is shown below. An additional series of MR exposures was produced in 2001, and finally in this example a series of exposures was produced in 2007. The year 2007 is the most current acquisition time period and the data in this year are automatically shown largest in the calling of the user interface. This is indicated in FIG. 3 where the column to the right takes up the most space in the presentation.

The image series are consequently characterized not only by a respective assessment parameter; rather, they are grouped in a chronologically clear manner. The parameter that is used for this is the acquisition date of the image information, i.e. the time parameter 11. Moreover, the images are also characterized by the type of the data acquisition. As was already explained, the data in the first row were acquired with the MR method 9. In contrast to this, the data in the second row were acquired with the PET method 8. Its presentation is analogous to that in Row 1. Additional methods are the PET-CT method and the pure CT method 7. A button 12 that indicates the imaging method 7, 8, 9 or the combination of these in the respective row is provided on the right side of the screen 3 for each row, i.e. for each presentation of the respective results. In this way it is also possible to hide a specific imaging method if the user desires this in order to be able to show the remaining images larger or in order to make the presentation clearer.

With the use of a pointer symbol 13, the user can make a selection on the screen with regard to the various parameters. If a button was selected, said parameters are shown emphasized in the shown embodiment of the invention. Since the year 2007 as the most recent year is selected by default, this year date is shown as a button 14 with a wide border.

Figure 4:
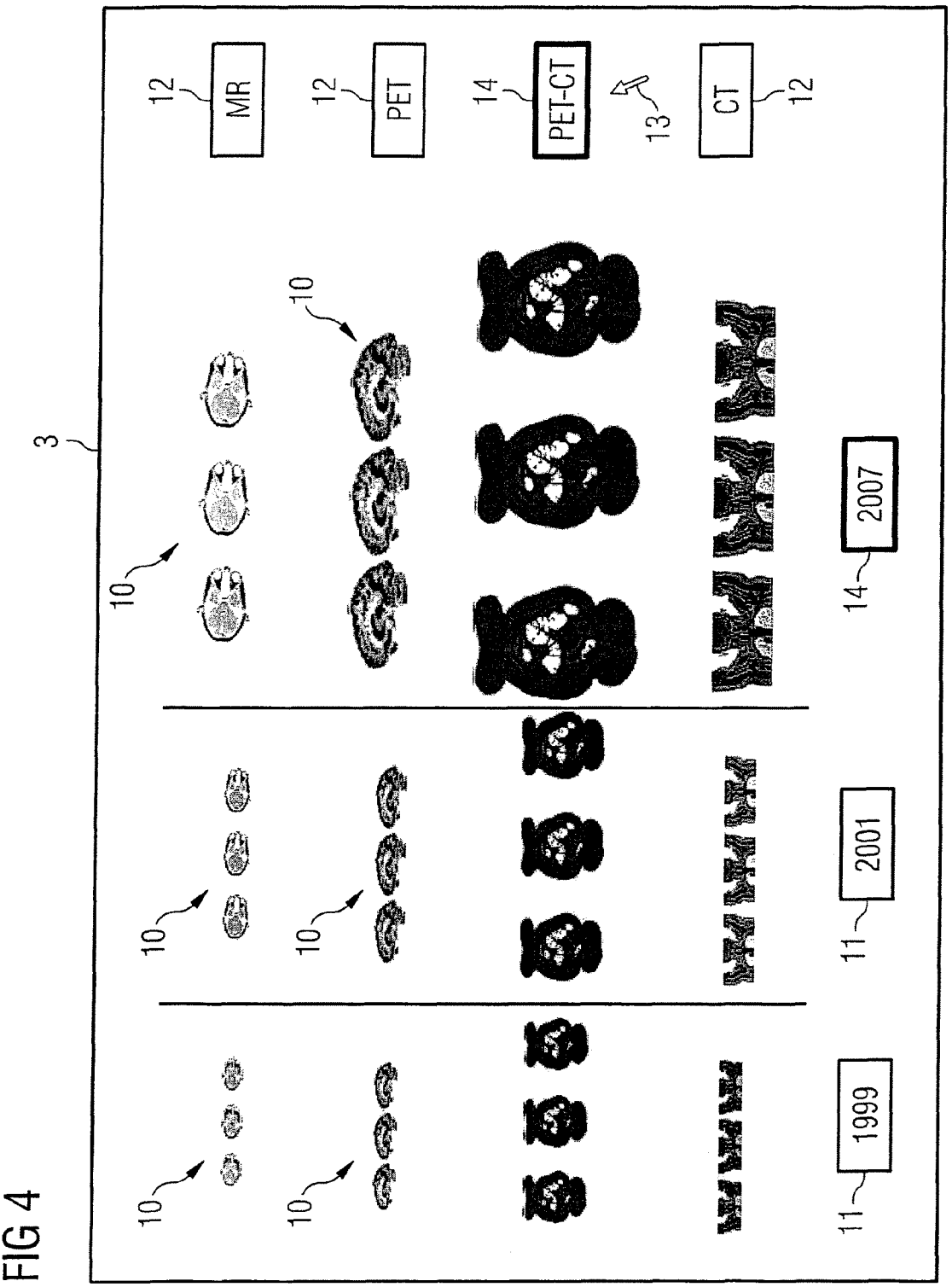

If the user would like to select a second display parameter in addition to the one display parameter in order to emphasize the corresponding images, he only needs to activate this second parameter with the pointer symbol 13. The result of such an activation is shown in FIG. 4. There (in 2007) the imaging method from PET 8 and CT 7 was selected, i.e. PET-CT. In the resulting presentation, the data symbols 10 of 2007 are emphasized and again under these the data symbols 10 with regard to PET-CT. A person therefore has a particularly large view with good resolution of the spatially resolved image information acquired with PET-CT in 2007. In this case both the button 14 for the year 2007 and the button 14 for PET-CT are accordingly emphasized.

Relative to the selected data symbols 10, the adjacent data symbols 10 are set in the background in terms of size, wherein they can even be entirely covered over given a too-dense population of the screen (not shown).

This principle can be expanded. The chronological sorting according to the point in time of the image acquisition is thus possible within an examination (given dynamic series). The chronological sorting according to calendar time units (for example months instead of years) is possible on one (horizontal or vertical) axis of the grid. The type of the imaging method (MR, CT, PET) can be presented on the other axis. The examined body regions (thorax, abdomen, pelvis ...) can be presented in different colors. Combinations are possible, for example with the examination type (routine, magnetic resonance cholangiography (MRCP), right hip ... ). Overall, measurement parameters can be adopted as display parameters; however, the latter can just as easily be set independent of the former.

The region to which the current attention of the user is applied is always shown emphasized. For example, the color or other parameters can be defined on a side palette such that here an emphasis is also possible. The setting of contrast and brightness etc. can also be used as display parameters.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for implementing a medical examination through a user interface of at least one medical imaging device, comprising the steps of:

via a user interface of a processor, manually selecting and entering a number of user-selected measurement parameters for operating the medical imaging device to implement a medical examination, including selecting the number of said measurement parameters;

in said medical imaging device, generating spatially resolved image information dependent on said number of measurement parameters, and storing said spatially resolved image information on a storage medium;

in a first display stage, accessing said image information from said storage medium and displaying said image information as multiple data symbols, comprising more than three data symbols, that represent but do not reveal said image information, in an initial arrangement on a single screen of said user interface in a display format that is predetermined from said number of measurement parameters, each of said multiple data symbols requiring a user entry via said user interface to reveal said image information;

in a second display stage following said first display stage, via said user interface, manually selecting and entering at least three display parameters that define a visual selected arrangement of said multiple data symbols on said single screen, said at least three display parameters including a time parameter; and in said processor, automatically controlling re-arrangement of said data symbols on said single screen depending on said manually selected and entered at least three display parameters to change said initial arrangement to said selected arrangement, including automatically emphasizing data symbols among said multiple data symbols that belong to a most recent year larger and with better resolution than data symbols that do not belong to said most recent year.

2. A method as claimed in claim 1 comprising arranging said data symbols on said screen dependent on three spatial dimensions of a miniature view, as said three display parameters.

3. A method as claimed in claim 1 comprising arranging said multiple data symbols in a grid using said three display parameters, and employing a time parameter as a first of said display parameters, employing an imaging device parameter as a second of said display parameters, and employing an examination parameter as a third of said display parameters.

4. A method as claimed in claim 3 comprising employing a point in time of an image acquisition as said time parameter to cause said multiple data symbols to be shown sorted in chronological order.

5. A method as claimed in claim 3 comprising employing, as said imaging device parameter, a parameter selected from the group consisting of parameters designating a type of said imaging device and setting parameters for said imaging device.

6. A method as claimed in claim 3 comprising employing, as said examination parameter, a parameter that designates an examined body region of a patient.

7. A method as claimed in claim 1 comprising influencing a position of a pointer symbol on said screen using an electromechanical transducer to select at least one of said data symbols and display parameters, with a size of said multiple display parameters on said screen being dependent on a distance thereof from said pointer symbol on said screen.

8. A method as claimed in claim 1 comprising causing said data symbols that belong to said most recent year to at least partially occlude adjacent data symbols.

9. A device for implementing a medical examination through a user interface of at least one medical imaging device, comprising:

a processor an input device allowing manual entry of a number of user-selected measurement parameters for operating the medical imaging device, operated by said processor, to implement a medical examination, including selection of said number measurement parameters;

said processor being configured to generate spatially resolved image information dependent on said number of measurement parameters;

a storage medium at which said spatially resolved image information is stored;

a display having a single display screen;

said processor being configured to access, in a first display stage, said image information from said storage medium and to present said image information as multiple data symbols, comprising more than three data symbols, that represent but do not reveal said image information, in an initial arrangement on said single display screen in a display format that is predetermined from said number of measurement parameters, each of said multiple data symbols requiring a user entry via said user interface to reveal said image information;

said input device also being configured to allow, in a second display stage following said first display stage, manual selection and entry of at least three display parameters that define a visual arrangement of said multiple data symbols on said single screen, said at least three display parameters including a time parameter; and said processor being configured to automatically control re-arrangement of said data symbols on said single display screen dependent on said manually selected and entered at least three display parameters to change said initial arrangement to said selected arrangement by, including automatically emphasizing data symbols among said multiple data symbols that belong to a most recent year larger and with better resolution than data symbols that do not belong to said most recent year.

10. A device as claimed in claim 9 wherein said input unit is configured to allow moving a position of a pointer symbol on said display screen using an electromechanical transducer to select at least one of said data symbols and display parameters, and wherein said processor is configured to set a size of said multiple display parameters on said display screen dependent on a distance thereof from said pointer symbol on said display screen.

11. A device as claimed in claim 9 wherein said processor is configured to cause said symbols that belong to said most recent year to at least partially occlude adjacent data symbols on said single display screen.

* * * * *